United States Patent

Plant Pat. 3,798

Patented Nov. 4, 1975

3,798

STRAWBERRY PLANT

Herschel L Boll, R.R. 4, Champaign, Ill. 61820

Filed Nov. 18, 1974, Ser. No. 524,762

Int. Cl. A01h 5/03

U.S. Cl. Plt.—48 1 Claim

ABSTRACT OF THE DISCLOSURE

My invention relates to a new and distinct variety of strawberry plant. It is the result of a cross of [(Canall × Twentieth Century) × Twentieth Century] × Ogallala, made by me in 1967, at Champaign, Ill.

Since my discovery of the original plant, I have asexually reproduced a large number of plants from the original mother plant by rooted runners.

My object in the asexual propagation of the original mother plant was to determine the characteristics of the plant and of its fruit by the testing of a large number of plants. The distinguishing features of my new variety have proved to be permanent. My new variety has proved itself to have unusual possibilities because of its high productivity even on very poor soil, its vigorous growth, its early season of maturity, and its large fruit that is medium dark red in color.

Figure 1:
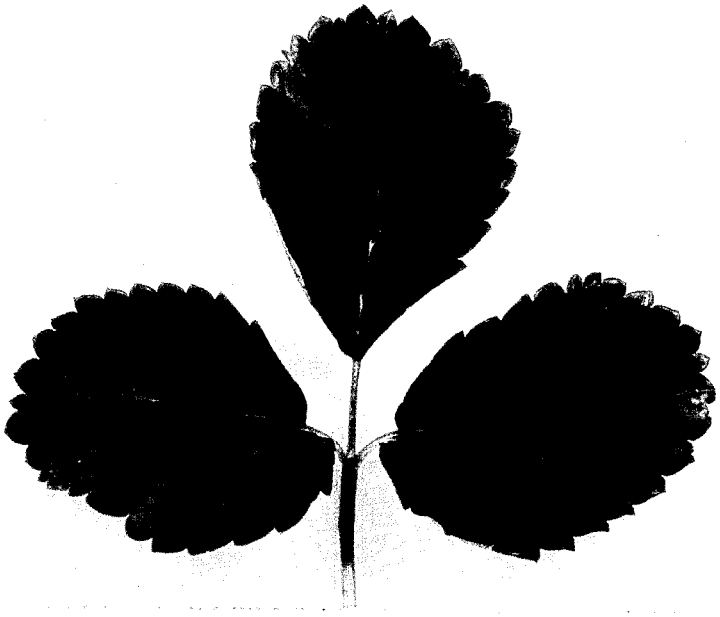
FIG. 1 shows a typical leaf in full color.
Figure 2:
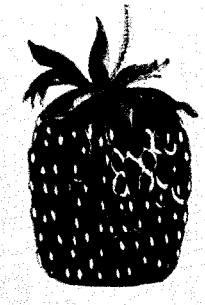
FIG. 2 is a primary berry of typical blunt-wedge shape with two furrows.
Figure 3:
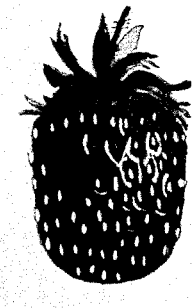
FIG. 3 illustrates a primary berry of typical round-wedge shape.
Figure 4:
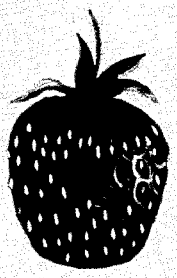
FIG. 4 shows a secondary berry of typical round-wedge shape.
Figure 5:
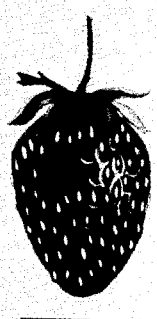
FIG. 5 is a secondary berry of typical long-conic shape.
Figure 6:
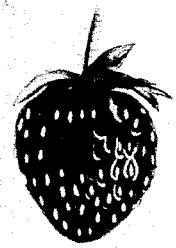
FIG. 6 illustrates a tertiary berry of typical conic shape.

In general, the distinct and new variety of strawberry plant, which is the subject of my invention and discovery, is characterized by its high productivity even on very poor soil, its vigorous growth, its early season of maturity, and its large fruit that is medium dark red in color. These characteristics I now refer to in greater detail. Color plate references are according to Color Standards and Color Nomenclature by Robert Ridgeway.

Under the conditions at Champaign, Ill., my new variety of plant is June-bearing and high in productivity, producing about one quart of fruit per plant planted. In southwestern Michigan, it even produced about ¾ quart of fruit per plan planted on very poor soil, "bank-run gravel" where few weeds would grow. The plants are vigorous and tall, measuring up to 14 inches in height and averaging about 10 to 12 inches. They produce a medium number of runners, making a moderately wide row.

The leaves are medium green in color, or are approximately Forest Green (Plate XVII), or varying from Varley's Green (Plate XVIII) to Forest Green (Plate XVII) to Cerro Green (Plate V), depending mainly on soil fertility, but also depending on other soil conditions, exposure, and weather and climatic conditions. The leaves are medium to large in size, slightly glossy to glossy, cupped, medium in rugosity, and slightly crinkled. In most varieties, the terminal leaflet overlaps the lateral leaflets. On the large mature leaves of my new variety, instead, there is a fairly wide space between these leaflets, mostly due to a long terminal petiolule, measuring up to one inch in length and averaging about ½ to ¾ inch. On these leaves, the lateral leaflets also do not overlap at the base of the leaf; however, the lateral leaflets have the normal short petiolules. A few leaves have 4 or 5 leaflets instead of the normal 3. The flowers are perfect. The date of the first blossoms in 1973 at Champaign, Ill. was April 29.

At Champaign, Ill., my new variety of strawberry plant begins to mature its fruit early and at about the same time as Premier (Howard 17) and Sunrise. The date of the first picking in 1973 at Champaign, Ill., was May 26. The harvesting period is medium in length, or 14 to 21 days. The berries are well formed throughout the bearing season.

The fruit is medium dark red (darker than Premier (Howard 17) and much darker than Sunrise), or is approximately Carmine Red (Plate I), or varying from Nepal Red (Plate I) to Carmine Red (Plate I) to Ox-blood Red (Plate I), depending mainly on exposure, but also depending on soil, weather, and climatic conditions. The fruit is large (larger than Sunrise), with the primary berries averaging about 1¼ to 1½ inches in diameter, and the size is maintained well during the picking season. The primary berries are blunt wedge to round wedge in shape, while secondary and later berries are mostly long conic, but vary from round wedge to long conic to conic. Some primaries have from one to four furrows. The largest berries of Premier (Howard 17) are furrowed on each side, forming "double" berries. The largest berries of my new variety do not appear as "double" berries. Berries of all shapes are slightly necked. The fruit is slightly glossy to glossy, firm, and attractive in appearance.

The calyx is large. Nearly half of the sepals are 3-toothed instead of single-toothed. The achenes are slightly raised, and are yellow to red depending on exposure.

Under the conditions existing where I have reproduced and tested my new variety of strawberry plant, the flesh of the berry is medium red. The fruit is relatively sweet, and is slightly above average in flavor.

My new variety of strawberry plant is not especially resistant to any of the diseases. The strawberry above described, and the plant producing it, of course, may vary in slight details, depending on soil, weather, and climatic conditions.

What I claim is:

1. A new and distinct variety of strawberry plant substantially as herein shown and described, characterized by its high productivity even on very poor soil, its vigorous growth, its early season of maturity, and its large fruit that is medium dark red in color.

No references cited.

ROBERT E. BAGWILL, Primary Examiner